US012165033B2

(12) United States Patent
Maaløe et al.

(10) Patent No.: US 12,165,033 B2
(45) Date of Patent: Dec. 10, 2024

(54) INTELLIGENT COMPUTER AIDED DECISION SUPPORT SYSTEM

(71) Applicant: Corti Aps, Copenhagen K (DK)

(72) Inventors: Lars Maaløe, Copenhagen K (DK); Andreas Cleve, Copenhagen K (DK)

(73) Assignee: Corti Aps, Copenhagen (DK)

( * ) Notice: Subject to any disclaimer, the term of this patent is extended or adjusted under 35 U.S.C. 154(b) by 453 days.

(21) Appl. No.: 17/614,256

(22) PCT Filed: May 28, 2020

(86) PCT No.: PCT/EP2020/064842
§ 371 (c)(1),
(2) Date: Nov. 24, 2021

(87) PCT Pub. No.: WO2020/239910
PCT Pub. Date: Dec. 3, 2020

(65) Prior Publication Data
US 2022/0240871 A1 Aug. 4, 2022

(30) Foreign Application Priority Data

May 28, 2019 (EP) .................................... 19177115
Jan. 17, 2020 (EP) .................................... 20152460

(51) Int. Cl.
*G06N 3/045* (2023.01)
*A61B 5/00* (2006.01)
(Continued)

(52) U.S. Cl.
CPC ........... *G06N 3/045* (2023.01); *A61B 5/4803* (2013.01); *G16H 40/20* (2018.01); *G16H 50/20* (2018.01);
(Continued)

(58) Field of Classification Search
CPC ........ G06N 3/045; G06N 3/044; G06N 3/047; G06N 7/01; G06N 5/04; G06N 3/084;
(Continued)

(56) References Cited

U.S. PATENT DOCUMENTS 10,152,970 B1 12/2018 Olabiyi et al.
11,410,637 B2 * 8/2022 Bonada ................ G10H 1/0008
(Continued)

FOREIGN PATENT DOCUMENTS

CN        108766419 A      11/2018
WO    WO-2021204641 A1 * 10/2021 ........... A61B 5/1117

OTHER PUBLICATIONS

Lars, M. , et al., "Biva: a Very Deep Hierarchy of Latent Variables for Generative Modeling", Arxiv.org, Cornell University Library, 201 Olin Library Cornell University Ithaca, NY 14853.
(Continued)

*Primary Examiner* — Hai Phan
*Assistant Examiner* — Ian Scott McLean
(74) *Attorney, Agent, or Firm* — Joseph C. Zucchero; Carolyn S. Elmore; Elmore Patent Law Group, P.C.

(57) ABSTRACT

The present invention relates to a method for assisting an interviewing party in deciding a response action in response to an interview between said interviewing party and an interviewee party. The method comprises providing a processing unit and inputting the voice of the interviewee party into the processing unit as an electronic signal, and processing the electronic signal by means of said processing unit in parallel with the interview taking place. The method further includes an anomaly routine comprising a statistically learned model, and by means of said statistically learned model determining a respective number of samples of said sequence of samples being an anomaly of said statistically learned model and returning to said anomaly routine for
(Continued)

processing a subsequent number of samples of said sequence of samples by said anomaly routine.

8 Claims, 5 Drawing Sheets

(51) Int. Cl.
    *G16H 40/20*     (2018.01)
    *G16H 50/20*     (2018.01)
    *G16H 80/00*     (2018.01)
    *H04M 3/51*     (2006.01)

(52) U.S. Cl.
    CPC .......... *G16H 80/00* (2018.01); *H04M 3/5116* (2013.01); *H04M 2203/555* (2013.01)

(58) Field of Classification Search
CPC .......... G06N 3/088; G06N 20/00; G06N 3/02; A61B 5/4803; A61B 5/00; A61B 5/747; A61B 7/003; G16H 40/20; G16H 50/20; G16H 80/00; G16H 10/20; G16H 40/67; H04M 3/5116; H04M 2203/555; H04M 3/527; H04M 2201/40; H04M 11/04; G06F 40/216; G08G 5/0017; G08G 5/0013; G08G 5/0026; G08G 5/0056; G06Q 10/10; G10L 15/16; G10L 13/027; G10L 25/84; G10L 25/30; G10L 25/66; H04W 4/90

See application file for complete search history.

(56) References Cited

U.S. PATENT DOCUMENTS

| | | |
|---|---|---|
| 2007/0003914 A1 | 1/2007 | Yang |
| 2016/0217789 A1 | 7/2016 | Lee et al. |
| 2018/0322961 A1 | 11/2018 | Kim et al. |
| 2019/0065486 A1 | 2/2019 | Lin et al. |
| 2019/0156944 A1 | 5/2019 | Eriksson et al. |
| 2021/0294845 A1* | 9/2021 | Bharitkar .............. G06F 16/683 |

OTHER PUBLICATIONS

Rushe, E., et al., "Anomaly Detection in Raw Audio Using Deep Autoregressive Networks", IEEE International Conference on Acoustics, Speech and Signal Processing (ICASSP)DOI: 10.1109/ICASSP. 2019.8683414 external link, 3597-3601.

* cited by examiner

INTELLIGENT COMPUTER AIDED DECISION SUPPORT SYSTEM

The present specification relates to a method of assisting an interviewing party by a computer such that the interviewing party may decide a response action faster or more reliable. A statistically learned model is contemplated for assisting the interviewing party.

The setting can be an emergency situation such as a car accident, a cardiac arrest or an air plane experiencing problems.

Another setting that is contemplated by the present specification may be a physician office visit where the patient and physician meet for the purpose of making decisions concerning patient care, i.e. a doctor's visit or a hospital ward round (visit to patients in hospital by medical staff for the purpose of making decisions concerning patient care).

In case of problems on an airplane such as engine failure, the cockpit communicates to a nearby tower about the problem, and the tower may advice or instruct on which actions are to be taken by the cockpit—for example if the airplane should return to the departure airport or make an emergency landing immediately if that is possible.

Typically, the communication is in the form of an interview taking place between the pilot in the cockpit (interviewee party) and an air traffic controller in the tower (interviewing party). The tower may ask the cockpit about the reading of cockpit dials such as oil pressure etc. The questions may be defined by a protocol and ordered in a sequence, which the tower follows in order to narrow down the problem. During the communication or interview, the tower may arrive at one or more instructions for the cockpit to follow.

It is contemplated to aid the tower with a computer system such that the proper instructions can be dispatched to the cockpit faster or that there is a higher chance that proper instructions are dispatched, i.e. that the instructions suit the problem experienced by the air plane.

The communication between the cockpit and tower is recorded preferably in real time and routed to the computer system's processing unit where it is processed using a statistical model in order to diagnose the problem, and determine the most likely cause of action in order to respond to a threat to the safety and operation of the airplane. The result is presented to the tower, which may or may not account for what the computer suggests.

In case of an emergency situation such as a cardiac arrest, a key component of providing proper care is to summon the emergency medical services (usually an ambulance), by calling for help using the appropriate local emergency telephone number (emergency call). Early recognition that a cardiac arrest has occurred is key to survival—for every minute a patient stays in cardiac arrest, their chances of survival drop.

The emergency call is received by a dispatcher at a public safety answering point (PSAP), i.e. an emergency call center. Similarly to the air plane experiencing problems, the dispatcher interviews or interrogates the caller in order to diagnose the emergency and determine if and what kind of emergency medical services should be dispatched.

It is contemplated that a computer system, which is similar to the one described for the airplane emergency may assist the dispatcher in order to arrive at a response action more quickly, i.e. the communication between the caller and dispatcher is recorded and routed to the computer system's processing unit where it is processed using a statistical model in order to diagnose the emergency, and determine an expected response action. The expected response action is presented to the dispatcher, who may follow the suggestions made by the computer system.

The response action may include which treatment is suitable or dispatching emergency medical services such as an ambulance and/or possibly providing a set of pre-arrival instructions to the caller in order for the caller to perform pre-arrival emergency medical service such as first aid in the case the caller is a bystander to the injured person having the medical emergency. Alternatively, that the injured person is instructed to seek medical assistance at the emergency room or at the local doctor's office. The response action may also be instructions to the cockpit.

The above objects and advantages together with numerous other objects and advantages, which will be evident from the description of the present invention, are according to a first aspect of the present invention obtained by:

A method for assisting an interviewing party in deciding a response action in response to an interview between said interviewing party and an interviewee party, said method comprising the steps of:

providing a processing unit and inputting the voice of said interviewee party into said processing unit as an electronic signal, processing said electronic signal by means of said processing unit in parallel with said interview taking place, said processing lasting the duration of said interview or until said response action being decided by said interviewing party, said processing including:

separating said electronic signal into a sequence of samples in the time domain or a domain representative of the frequency contents of said electronic signal, said processing further including:

a) an anomaly routine comprising a statistically learned model, and by means of said statistically learned model determining:

a respective number of samples of said sequence of samples being an anomaly of said statistically learned model or said respective number of samples being a normality of said statistically learned model, b) when said respective number of samples being determined as an anomaly of said statistically learned model:

returning to said anomaly routine for processing a subsequent number of samples of said sequence of samples, c) when said respective number of samples being determined as a normality of said statistically learned model:

providing an audio recognition model and detecting an audio feature of said respective number of samples by means of said audio recognition model, providing an action prediction model and analyzing said audio feature by means of said action prediction model for determining an expected response action, providing a display or a speaker, and presenting said expected response action to said interviewing party by means of said display or said speaker for assisting said interviewing party, returning to said anomaly routine for processing a subsequent number of samples of said sequence of samples by said anomaly routine.

The action prediction model or analyzing model may be part of an action prediction routine and constitute a diagnosis routine for determining the response action.

The response action may also be determined by means of a lookup table associating diagnoses and response actions.

The result of the action prediction routine (diagnosis) may be a response action, or if the right question has been asked, or a suggestion to a question to be asked, or which symptoms describe the situation in general.

An anomaly may be explained by a data point that is outside of the probability distribution of the data that the statistical model is learned upon, i.e. that the data point being an unlikely event.

The statistical model may be constructed such that it encodes or transforms the input signal into a latent probability distribution for example by means of a neural network. The latent distribution may be constituted by a lower dimensionality than that of the probability distribution of the input signal. Samples from the latent distribution may then be decoded back into an approximation to the distribution of the input signal through a second statistical model, i.e. a decoder, which may also be in the form of a neural network.

The latent distribution may be conditioned on a known prior distribution during the learning procedure, hence an approximation to the true latent distribution is known. The combination of the latent distribution, prior distribution and the approximation to the input distribution can be collected into an approximation to the confidence. When computing this approximation from an input data point, it explains how well this data point is represented in the data set that the statistical models were learned from. If the difference exceeds a certain threshold, the data point is classified as an anomaly.

The audio feature may be speech, noise or sounds such as breathing patterns.

The respective number of samples may be a first number of samples, which is not to be understood as the samples representing the interviewees voice in the first part of the interview, but may be one or more samples representing the interviewees voice in a window a bit into the interview, for example the respective number of samples may represent a window of 2 ms, which occurs 1 second into the interview.

The processing may also be terminated at a fixed time after the interview is initiated, for example between 2-10 minutes into the interview the processing may be terminated. Alternative between 2-8 minutes or 2-5 minutes or 3-8 minutes.

The number of samples constitute information in the form of real data or production data, i.e. data that the statistically learned model processes during execution of the method (the data is processed according to the set of instructions defined by the method).

The interviewing party interviews the interviewee party by asking questions to the interviewee party, and the method continuously determines if the voice of the interviewee party comprises reliable information that may be processed in order to return a reliable output. The reliable information is processed continuously, and any noise is skipped. In this way, noise may be excluded from the processing, which may increase the speed of the processing and the reliability of the output. In the present context noise is to be understood as audio, which deviates from the audio used in the training of the statistically learned model in such a degree that the statistically learned model would not return a useful output.

In line with the present invention, the interviewing party may be an air traffic controller in an air traffic control tower, or a dispatcher at a public safety answering point or a medical professional on a hospital ward round.

Correspondingly, the interviewee party may be a pilot in the cockpit of an airplane experiencing problems, or a person involved in an accident such as a car accident, or a patient at a hospital.

The purpose of the interview is to collect information from the interviewee party in order to diagnose the problem and decide a response action based on the collected information, and the experience of the interviewing party.

The processing unit operates in parallel with the interview, and processes the audio signal representing the voice of the interviewee party. The processing may determine the words spoken by the interviewee party, and may diagnose the problem based on the recognized words in order to determine the response action.

The processing unit determines the response action independently or without interaction from the interviewing party, and presents the response action to the interviewing party. The response action determined by the processing unit is an expected response action, because it is based on learned data and the data collected from the interview.

The processing unit may be part of a system, which may include a number of microphones for recording the voice of the interviewing party and/or the interviewee party. The system may as well comprise the display and/or speaker for presenting the expected response action to the interviewing party.

The voice may be sampled in connection with the recording of the voice. The sampling may be at 16 kHz, which is useful for human speech.

The system may also incorporate a telecommunications network in the case that the interviewing party and the interviewee party are located at a distance from each other—such as in an air traffic control tower and a cockpit of an airplane.

The telecommunications network may be a telephone or satellite network connecting the communication terminals of the interviewing party and the interviewee party respectively.

The voice of the interviewee party may be recorded with a microphone at the interviewee party's location and converted to an electronic signal, which may be transmitted wired or wirelessly to the communications terminal of the interviewing party, and routed into the processing unit. The microphone may be associated with the interviewee party's communication's terminal such as a telephone or headset.

The voice of the interviewing party may also be processed by the processing unit in order for the processing unit to determine an expected response action. The voice of the interviewing party may be recorded by a microphone, converted to an electronic signal, and routed into the processing unit.

In case the interviewing party and the interviewee party are in the same room such as in the case of a hospital ward round, it is contemplated that the conversation/interview may be recorded using a microphone. The microphone may be connected to a terminal of a portable computer such a laptop or tablet computer, which the medical professional may carry during the hospital ward round or at the physician office visit. Again, the system may assist the medical professional by suggesting an expected diagnose such that the medical professional may decide faster or more reliably on the type of treatment or care of the patient.

The term assisting in the present context means that the interviewing party receives information from the system in order to help deciding on a response action, which the interviewing party may or may not use or take advantage of during the emergency call.

Thus, the interviewing party decides on the response action, but gains information from the system in order to help deciding on a response action. Alternatively, the system may propose a response action for the interviewing party to approve.

A statistically learned model may be a hidden Markov model or a neural network (artificial neural network), and it may be trained with training data in order to find a predictive function, which associates an input and an output.

The training data are samples from the probability distribution according to which the input and output are distributed. The statistically learned model is trained such that the predictive function associates the input and output with the smallest error as possible, i.e. a loss function is defined and minimised.

An anomaly routine/detection is a test of whether or not the respective interval is an outlier/anomaly of the distribution that the statistically learned model has been trained from, i.e. it is tested if the samples used to train the statistically learned model are also representative of the samples that are provided during live execution of the system (the respective number of samples).

If the respective number of samples is an outlier/anomaly, the statistically learned model will not result in a useful output—it can be said that the statistically learned model had then been trained with too few training samples, which are not representative of the number of samples such that a useful output can be expected.

A number of samples are to be understood as a set or collection of samples wherein the samples follow each other chronologically in time. Thus, the number of samples represents a time series or signal, which is an interval or window of the whole interview—the window may be as small as a single sample.

Each sample may be represented as an integer or a real number.

The processing unit may operate on one sample at a time, i.e. the number of samples being a single sample such that the single sample may constitute the input to the statistically learned model.

Alternatively, a plurality of samples may constitute the input to the statistically learned model. The plurality of samples may comprise one or more samples, which are new (has not been processed previously), and one or more samples, which has been processed previously.

A sequence of samples is to be understood as samples following each other in time—resulting from the voice of the interviewee party being sampled.

A subsequent number of samples is to be understood as a number of samples with the first sample starting at a later point in time than the first sample of the previous number of samples.

According to a second aspect of the present invention, the above objects and advantages are obtained by:

A system for assisting an interviewing party in deciding a response action in response to an interview between said interviewing party and an interviewee party, said system comprising:
- a receiver for receiving the voice of said interviewee party and presenting the voice of said interviewee party as an electronic signal,
- a processing unit for processing said electronic signal unit in parallel with said interview taking place, said processing lasting the duration of said interview or until said response action being decided by said interviewing party,
- said processing including separating said electronic signal into a sequence of samples in the time domain or a domain representative of the frequency contents of said electronic signal,
- said processing unit comprising:
  a) an anomaly routine including a statistically learned model for determining:
     a respective number of samples of said sequence of samples being an anomaly of said statistically learned model or
     said respective number of samples being a normality of said statistically learned model,
  b) a loop for returning to said anomaly routine for processing a subsequent number of samples of said sequence of samples when said respective number of samples being detected as an anomaly of said statistically learned model,
  c) an audio recognition model, and a diagnosis model for respectively detecting speech of said respective number of samples, and diagnosing said audio feature for determining an expected response action to said interview when said respective number of samples being detected as a normality of said statistically learned model,
- said system further comprising:
  a feedback unit for presenting said expected response action to said interviewing party.

The receiver may be a microphone for converting the voice of the interviewee party from sound into an electronic signal, or a telephone for receiving the voice of said interviewee party as an electronic signal.

According to a third aspect of the present invention, the above objects and advantages are obtained by:

A method of assisting an interviewing party in deciding a response action in response to an interview between said interviewing party and an interviewee party:
- providing a processing unit and inputting the voice of said interviewee party into said processing unit as an electronic signal,
- processing said electronic signal by means of said processing unit in parallel with said interview taking place, said processing lasting the duration of said interview or until said response action being decided by said interviewing party,
- said processing including:
- separating said electronic signal into a sequence of samples in the time domain or a domain representative of the frequency contents of said electronic signal,
- said processing further including:
  a) an audio recognition routine including an audio recognition model for detecting an audio feature of a respective number of samples of said sequence of samples by means of a first statistically learned model, said audio recognition routine returning a first audio output representing the detected audio feature of said respective number of samples,
  b) an action prediction routine including a analyzing model for analyzing said first audio output by means of a second statistically learned model, said action prediction routine returning a feedback to said interviewing party,
  returning to said audio recognition routine and said action prediction routine for processing a respective subsequent number of samples of said sequence of samples by said audio recognition routine and said action prediction routine for determining an expected response action based on said respective interval and said respective subsequent interval, and presenting said expected response action to said interviewing party by means of a display or a speaker.

According to a fourth aspect of the present invention, the above objects and advantages are obtained by:

A method for generating information such as an image or speech, comprising:
- providing a storage unit storing a set of instructions, and a processing unit for executing said set of instructions,
- said set of instructions including a generator routine having a decoder constituted by a statistically learned model,
- said decoder being defined by an observable variable and a decoder hierarchy of a set of random variables, said decoder hierarchy constituted by layers having at least one random variable from said set of random variables in each layer,
- said observable variable, and said set of random variables being jointly distributed according to a prior probability distribution,
- said prior probability distribution being factorized having:
  - a first factor defined as a first probability distribution of said observable variable conditioned on said set of random variables,
  - a second factor defined as a second probability distribution of the random variable of the top layer of said decoder,
  - a third factor defined as the product of sequence of the probability distributions for the random variables of said set of random variables,
  - the random variable of each respective element in said product of sequence being conditioned on the random variables in the higher layers,
- said method further comprising sampling a value of the random variable of the top layer, and processing said value through said hierarchy such that said information is generated.

According to a fifth aspect of the present invention the above objects and advantages are obtained by:

A method for recognizing information such as speech or text, comprising: providing a processing unit,
- inputting said information into said processing unit as an electronic signal, and processing said electronic signal,
- said processing including a recognizing routine having an encoder constituted by a statistically learned model,
- said encoder being defined by an observable variable and an encoder hierarchy of a set of random variables, said encoder hierarchy constituted by layers,
- the random variables of said set of random variables being divided into a bottom-up path and top-down path through said encoder hierarchy,
- said set of random variables being conditionally distributed on said observable variable according to a probability distribution for approximating a posterior probability distribution,
- said probability distribution being factorized having:
  - a first factor defined as a first probability distribution of the random variable of the top layer of said encoder conditioned on said observable variable and the respective random variable of said bottom-up path below the top layer,
  - a second factor defined as the product of sequence of the products between the probability distributions for the random variables of said bottom-up path and the probability distributions for the random variables of said top-down path,
  - the respective random variable of said bottom-up path for a given index in the product of sequence being conditioned on said observable variable and the respective random variable of said bottom-up path for a lower index than said given index,
  - the respective random variable of said top-down path for a given index in the product of sequence being conditioned on:
    - said observable variable,
    - at least one respective random variable of said bottom-up path,
    - the respective random variable of said top-down path for a higher index than said given index,
- said processing further including passing said information through said encoder hierarchy, and outputting recognized information.

According to a sixth aspect of the present invention, the above objects and advantages are obtained by:

A method for determining when a data point being an anomaly, comprising providing a processing unit,
- inputting said data point into said processing unit as an electronic signal, and processing said electronic signal,
- said processing including a statistically learned model having an encoder, and a decoder,
- said encoder having an encoder hierarchy and said decoder having a decoder hierarchy, said encoder hierarchy and said decoder hierarchy being defined by a set of random variables, the random variables of said set of random variables being divided into a bottom-up path and a top-down path,
- said encoder hierarchy and said decoder hierarchy constituted by layers having at least one random variable from said set of random variables in each layer,
- said encoder defining a first probability distribution for approximating a posterior probability distribution, and said decoder defining a prior probability distribution,
- defining an evidence lower bound function being a function of said first probability distribution for random variables from said set of random variables including more random variables from the top layers than from the bottom layers,
- said evidence lower bound function further being a function of said prior probability distribution for random variables from said set of random variables including more random variables from the top layers than from the bottom layers,
- said method further comprising determining by means of said statistically learned model:
  - said data point being an anomaly of said statistically learned model when said evidence lower bound function being integrated to a value less than a threshold,
  - said data point being a normality of said statistically learned model when said evidence lower bound function being integrated to a value less than a threshold.

BRIEF DESCRIPTION OF THE FIGURES

The invention will now be explained in more detail below by means of examples of embodiments with reference to the very schematic drawing, in which.

The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout. Like elements will thus, not be described in detail with respect to the description of each figure.

Figure 1:
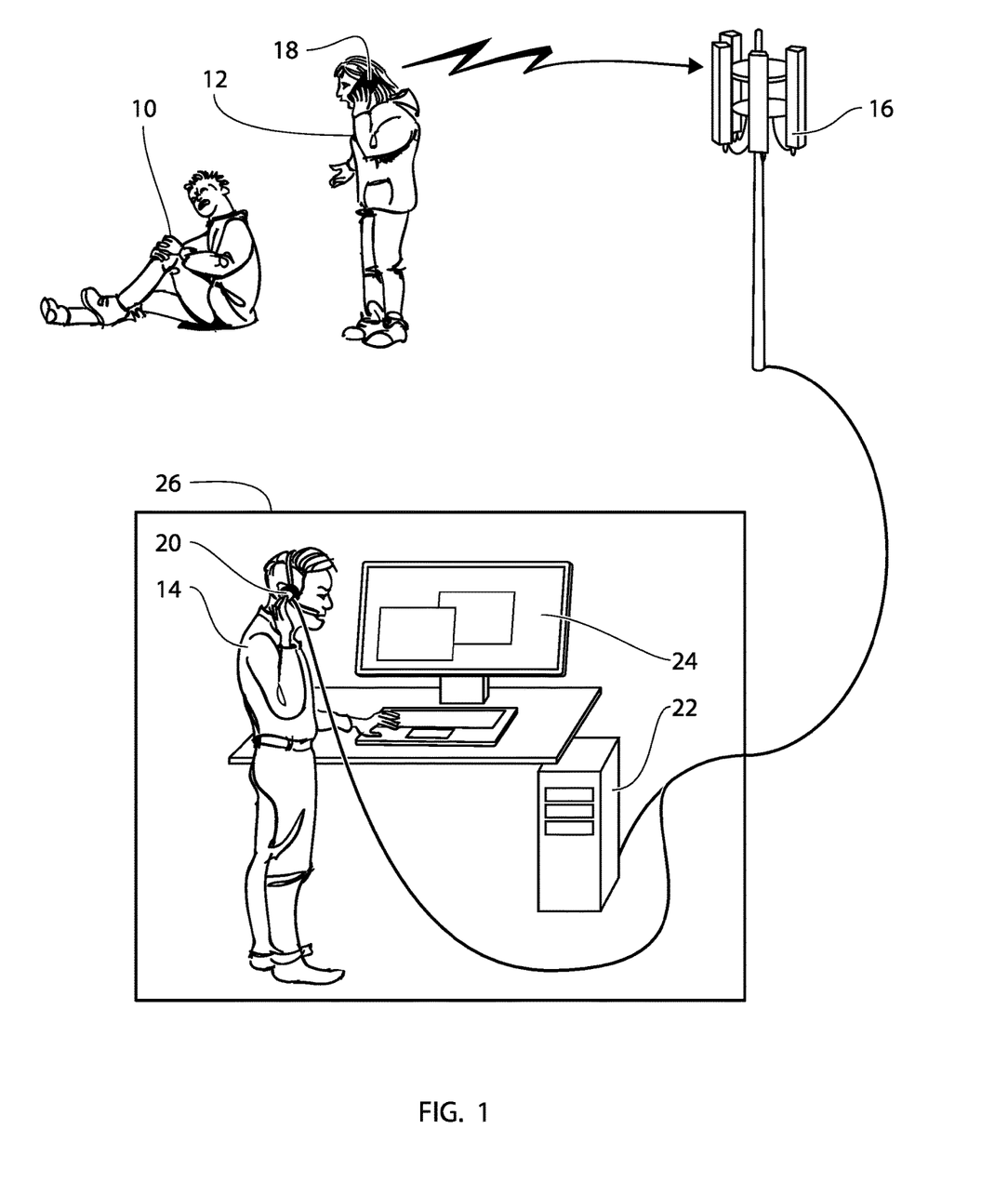
FIG. 1 shows a medical emergency and a public safety answering point.

FIG. 1 shows a medical emergency and a public safety answering point.

An injured person 10 is experiencing an acute injury or illness and is illustrated as laying on the ground.

A caller 12 is a bystander and is in need of assistance in order to help the injured person 10 experiencing the medical emergency in the form of an acute injury or illness.

The caller (interviewee party) 12 is illustrated using a mobile phone 18 for calling the emergency telephone number (emergency call).

The emergency call is transmitted through a public switched telephone network having a cell tower 16, and routed to a public safety answering point 26.

The emergency call is received at the public safety answering point as an electronic signal (electric current that represents information). The electronic signal may either be analog or digital.

A medical call taker (interviewing party), which is termed a dispatcher 14 in the following, answers the emergency call and a conversation between the caller and the dispatcher begins. A receiver 20 (such as a telephone possible including a handset for the dispatcher) may be used to answer the emergency call and transform the electronic signal to sound by means of a loudspeaker.

During the emergency call, the dispatcher follows the protocol for a systematized caller interrogation.

The protocol for a systematized interview may include questions in sequential order in order to determine the type of assistance needed. The protocol may be stored by the processing unit, and the sequence of questions of the protocol may be rearranged by the processing unit based on the information identified in the processing—for example certain cues or background noise may have a correlation or be associated with certain emergency situations, which means that the processing unit may present questions relating to such an emergency situation sooner than the interviewing party may realize be or she should ask questions relating to such an emergency situation.

At a point in time during the conversation, the dispatcher decides on a response action, which typically includes dispatching emergency medical services such as an ambulance and providing a set of pre-arrival instructions to the caller.

The electronic signal is also routed to a processing unit 22, i.e. a computer associated with the public safety answering point. The processing unit includes a set of instructions (algorithm) for processing the electronic signal.

Figure 2:
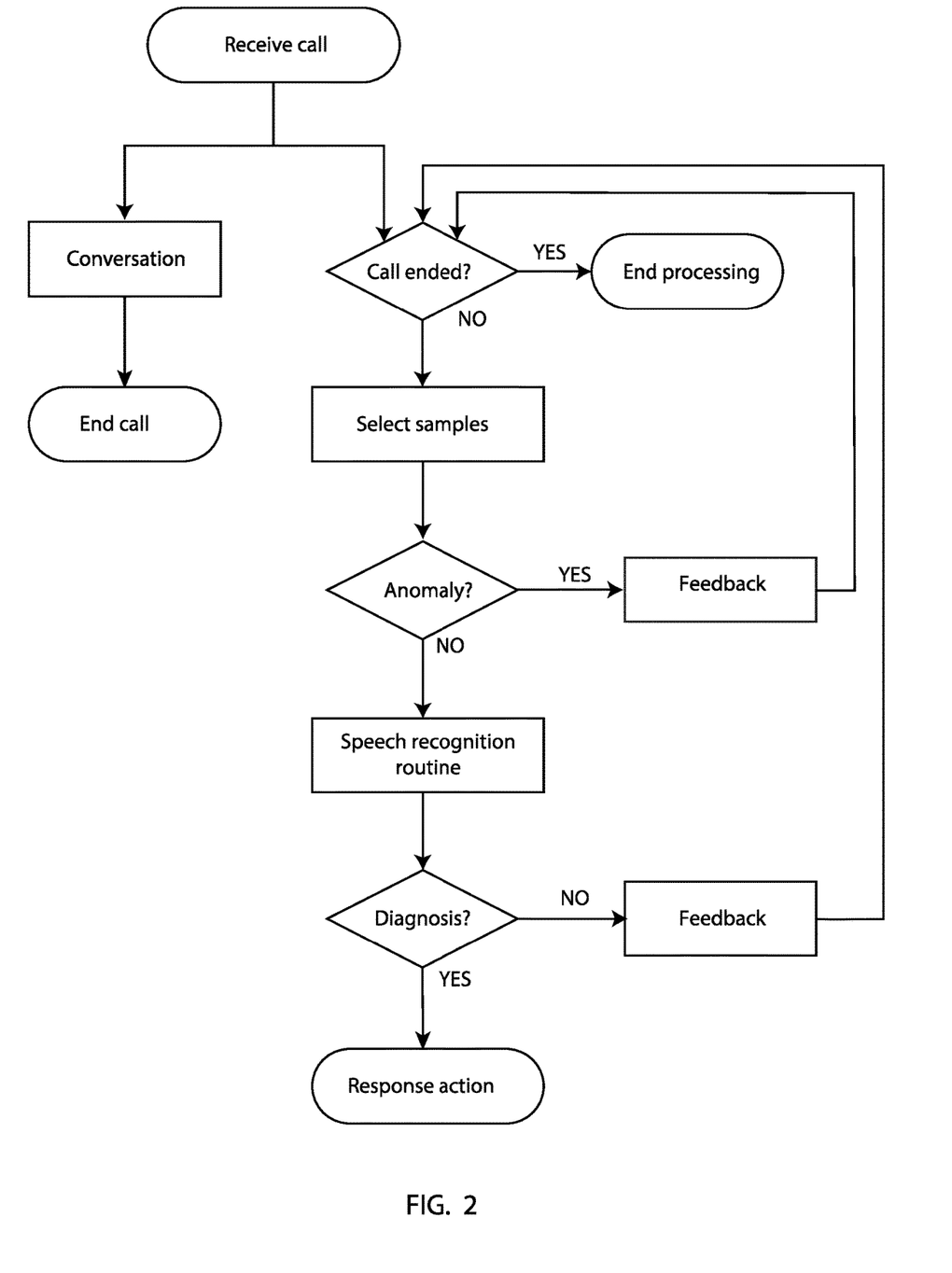
FIG. 2 shows a flowchart for assisting a medical call taker.

FIG. 2 shows a flowchart for a method of assisting an interviewing party such as an emergency dispatcher or an air traffic controller or a medical professional (doctor/nurse).

During the interview, the electronic signal is continuously routed or passed to the processing unit as long as the call/interview takes place, and the processing of the electronic signal lasts for the duration of the interview.

However, the processing may be aborted when the dispatcher/interviewing party has decided on a response action such as dispatching an ambulance to the scene of the accident—or when the caller/interviewee party has hung up.

The first number of samples is selected and passed to an anomaly routine, which is further described in connection with FIG. 3. The first number of samples may be constituted by a number of samples between 1 and 300 samples or even up to 1000 samples.

Figure 3:
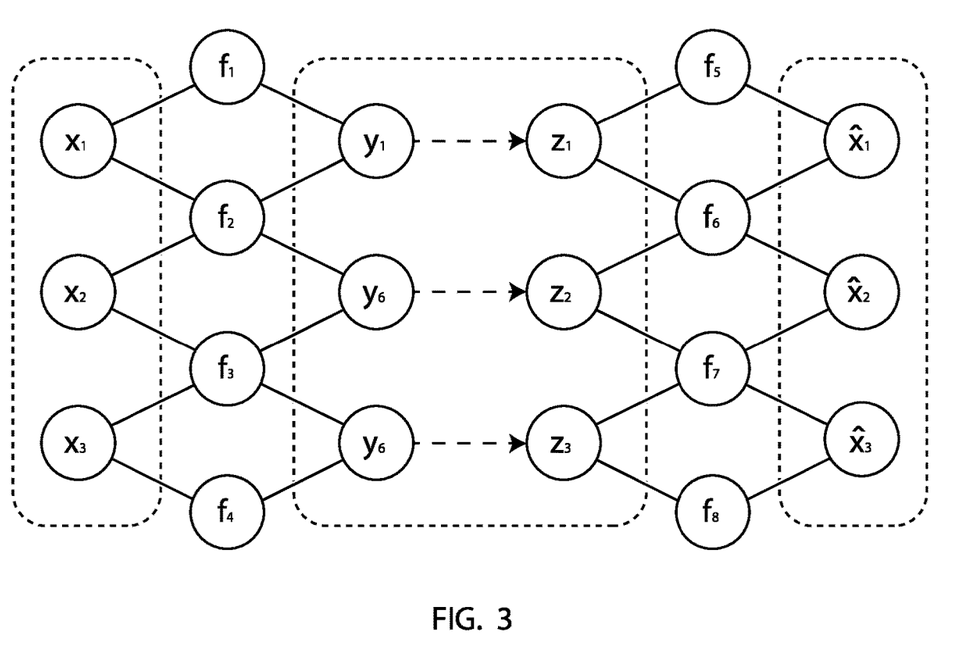
FIG. 3 shows a schematic of a system for assisting a medical call taker.

FIG. 3 shows a schematic of an exemplary part of an anomaly routine.

The anomaly routine determines if an interval is an anomaly or not. If it is not an anomaly, it is said to be a normality.

The anomaly routine comprises a statistically learned model, which may be a hidden Markov model or a neural network.

The statistically learned model is trained with training data in order to find a predictive function, which associates an input and an output.

The training data are samples from the probability distribution according to which the input and output are distributed.

The statistically learned model is trained such that the predictive function associates the input and output with the smallest error as possible, i.e. a loss function is defined and minimised.

FIG. 3 illustrates two examples of neural networks. The left hand side neural network is illustrated with three inputs $(x_1, x_2, x_3)$, i.e. the input layer has three input nodes. The left hand side neural network is further illustrated with three outputs $(y_1, y_2, y_3)$, i.e. the output layer has three output nodes.

Between the input layer and the output layer of the left hand side neural network is illustrated a single layer (one hidden layer). The inputs and outputs are connected to each other via the single layer. Each node in the single layer may have a function f, for example a tan h function with a certain amplitude/constant in front of the function.

The right hand side neural network illustrated in FIG. 3 has the same structure as the left hand side neural network. The input to the right hand side neural network is the output from the left hand side neural network.

The two neural networks illustrated in FIG. 3 are examples of neural networks, but illustrate the setup of a statistically learned model used in the anomaly routine in order to determine if a respective number of samples is an anomaly or a normality.

Thus, in the processing of the first number of samples by the anomaly routine, a first neural network (encoder/inference model/recognizing model) and a second neural network (decoder/generator) may be used in order to determine if a respective number of samples are an anomaly or a normality.

The first neural network may constitute a audio recognition neural network, and the second neural network may constitute a reversing neural network, i.e. a neural network that may reverse the prediction of the first neural network—predicting the input to the first neural network from the output of the first neural network.

The audio recognition neural network may be constituted by a recurrent neural network, which may use previously recognized letters in a word to estimate the following letter in the word.

The input of the first neural network is defined by the input vector $\bar{x}$, i.e. the input of the statistically learned model.

If a respective first number of samples represent 20 ms audio sampled at 16 kHz, the respective number of samples is 320, and the first neural network may have 320 inputs (320 input nodes—one for each sample).

The number of hidden layers and the number of hidden nodes in total should be chosen such that the neural network is not under or over fitted. These numbers may be chosen as a function of the number of samples used to train the neural network, and the number of input and output nodes.

The first neural network may be defined by a matrix with up to 50 million elements.

The output of the first neural network is defined by the output vector $\bar{y}$, which may have 320 output nodes.

The outputs of the first neural network in the anomaly routine may constitute the inputs of the second neural network, i.e. the input vector $\bar{z}$ of the second neural network. For such a constitution, and in the case that the output layer of the first neural network has 320 outputs as exemplified above, the input layer of the second neural network may have 320 inputs.

The second neural network may be defined by a matrix with up to 130 million elements.

The output of the second neural network is defined by the output vector $\hat{x}$.

Anomaly Routine:

The anomaly routine may compare the input vector $\bar{x}$ and the output vector $\hat{x}$. If these two vectors do not compare, it is determined that the respective number of samples is an anomaly—or that the respective number of samples represents a signal/information that is an anomaly. If these two vectors do compare, it is determined that the respective number of samples is a normality.

In other words, it is tested if the training samples (training data) used to train the statistically learned model are also representative of the respective number of samples (real/production data), i.e. if the respective number of samples is an outlier of the distribution that the statistically learned model has been trained from—for example if the signal to noise in the real data is too low or if the pronunciation deviates to a degree that it cannot be recognized in view of the data that the statistically learned model was trained with.

If the respective number of samples is an outlier, the statistically learned model will not result in a useful output—it can be said that the statistically learned model had then been trained with too few training samples, which are not representative of the respective number of samples such that a useful output can be expected.

The comparison of vectors may comprise determining the correlation between the input vector $\bar{x}$ and the output vector $\hat{x}$.

The correlation or difference between the input and output of the statistically learned model and the output vector $\hat{x}$ may be compared to a threshold, i.e. if the correlation or difference is above or below the threshold value, the respective number of samples is normality or an anomaly.

If the correlation is for example between 0 and 0.5, it is determined that the respective interval is an anomaly. If the correlation for example is greater than 0.5, it is determined that the respective number of samples is a normality.

As an alternative or addition to the above, the anomaly test/routine may include comparing the probability distribution of the training data with the probability distribution of the real data (the respective number of samples).

In case the probability function of the training data is unknown or of high dimensionality, the training data may undergo a transformation in order to reduce the dimensionality such that the probability function of the training data may be represented for example by a one-dimensional probability distribution (such as an exponential function in one dimension).

The transformation may be linear or nonlinear. A neural network may be used to reduce the dimensionality, i.e. to perform the transformation.

The probability distribution of lower dimensionality may be a prior given distribution (such as a Gaussian or exponential function in for example one dimension with defined parameters), and the transformation function may be trained to transform the probability function of the training data into the defined probability distribution of lower dimensionality. The same transformation function may be used as the basis for transforming the probability distribution of the respective number of samples. The lower dimensionality probability distribution of the respective number of samples may then be compared to the lower dimensionality probability distribution of the training data.

The comparison of probability distributions (whether in high or low dimensionality) may be done with an integration over the two probability distributions and comparing the integral to a threshold. If the integral is below the threshold, it may be decided that the respective number of samples represents an anomaly.

As another alternative or in addition, the test for a respective number of samples being an outlier/anomaly or not may comprise determining how far the respective number of samples is from the average of the probability distribution of the training data, i.e. the probability distribution defining the statistically learned model. For example, if the distance is more than 0.5 standard deviation away, it may be decided that the respective number of samples is an anomaly.

The respective interval may be Fourier transformed to the frequency domain, and the frequencies of the signal represented by the respective number of samples may constitute the input to the statistically learned model used by the anomaly routine, i.e. the signal represented by the respective number of samples may be divided into frequencies according to the energy at the frequencies of the respective interval.

Returning to the exemplary flowchart of FIG. 2, the processing returns feedback to the interviewing party in case the respective number of samples, which has been processed by the anomaly routine, turns out to be an anomaly.

The feedback may constitute negative feedback in the sense that the interviewing party is informed that the processing is ongoing. The feedback may be by sound or displayed on a display 24.

Alternatively, the method may not provide feedback to the interviewing party until either it returns a suggestion to a response action or until the processing reaches a number of samples that represent a signal, which is not an anomaly.

The processing may then continue with the next number of samples (window) representing the part of the interviewee's voice following the previous number of samples, which was an anomaly. Thus, the method loops back to the anomaly routine—possibly while the condition that the emergency call is still ongoing is fulfilled.

In case the respective number of samples, which have been processed by the anomaly routine, turns out not to be an anomaly, the processing may then continue with that respective number of samples, which may be passed on to an audio recognition routine for recognizing audio in the respective interval.

The audio recognition routine may already have been performed in connection with the anomaly routine, i.e. the first neural network of the anomaly routine is a neural network for audio recognition—the audio recognition routine may comprise a audio recognition neural network corresponding to the first neural network also used by the anomaly routine so that there is compliance between the test performed by the anomaly routine and the audio recognition routine.

The audio recognition routine determines the letters spoken by the interviewee party, and combines the letters to words.

The recognized audio, the word(s), of the respective number of samples are passed to a diagnosis routine for diagnosing the emergency.

The diagnosis routine may comprise a diagnosis neural network.

It may be necessary with audio from more than one set of samples in order to arrive at a diagnosis and for the method to propose a response action.

However, only a few set of samples, such as only one set of samples, which has been through the audio recognition and diagnosis routines, may lead to positive feedback in the form of one or more hints or suggestions to the interviewing party—alternatively in the form of rearranging the protocol for a systematized caller interrogation, i.e. rearranging the order of the list of questions in the protocol such that the probability of the interviewee party faster asking the right question(s) with respect to a certain emergency situation— the feedback to the interviewing party may include such rearrangement of the protocol's questions.

When enough audio has been recognized in order for the diagnosis routine to diagnose based on the recognized words, a response action is proposed to the dispatcher.

The processing may include a test similar to the anomaly routine in which it is tested if there is enough information available to the diagnosis routine in order to diagnose, i.e. that it can be expected that the diagnosis routine returns a diagnosis and corresponding response action that is correct/probable.

Background Noise and Cues.

The audio recognition and diagnosis routines may also analyse and/or respond to background noise, i.e. a specific background noise may be indicative of a certain emergency situation. The processing may identify such a specific background noise before the interviewing party, and thereby decrease the response time.

A neural network for audio event classification may be used in order to identify background noise, such as a breathing pattern and diagnose based on the identified background noise. It may be a dedicated neural network in that the training data may represent a specific audio event, i.e. the training data may be constituted by recordings of the sound of breathing of a number of people (such as 1000 people) experiencing a heart attack.

The diagnosis routines may also analyse and/or respond to special cues such as specific words, which may have been observed as having a high correlation with certain emergencies or physical conditions. A special word may be help, heart attack, engine failure etc. A dedicated neural network may be used for diagnosing special cues, and the dedicated neural network may be trained with data representing special cues.

Furthermore, the amplitude and/or frequency of the voice of the interviewee party may also be analysed in the processing. For example, a high amplitude may be indicative of the need for quickly dispatching an ambulance to the scene of the accident.

The processing may include a language routine for determining the language of the caller. The language routine may comprise a language neural network. The language routine may initialise immediately as the emergency call is received at the public safety answering point.

Figure 4:
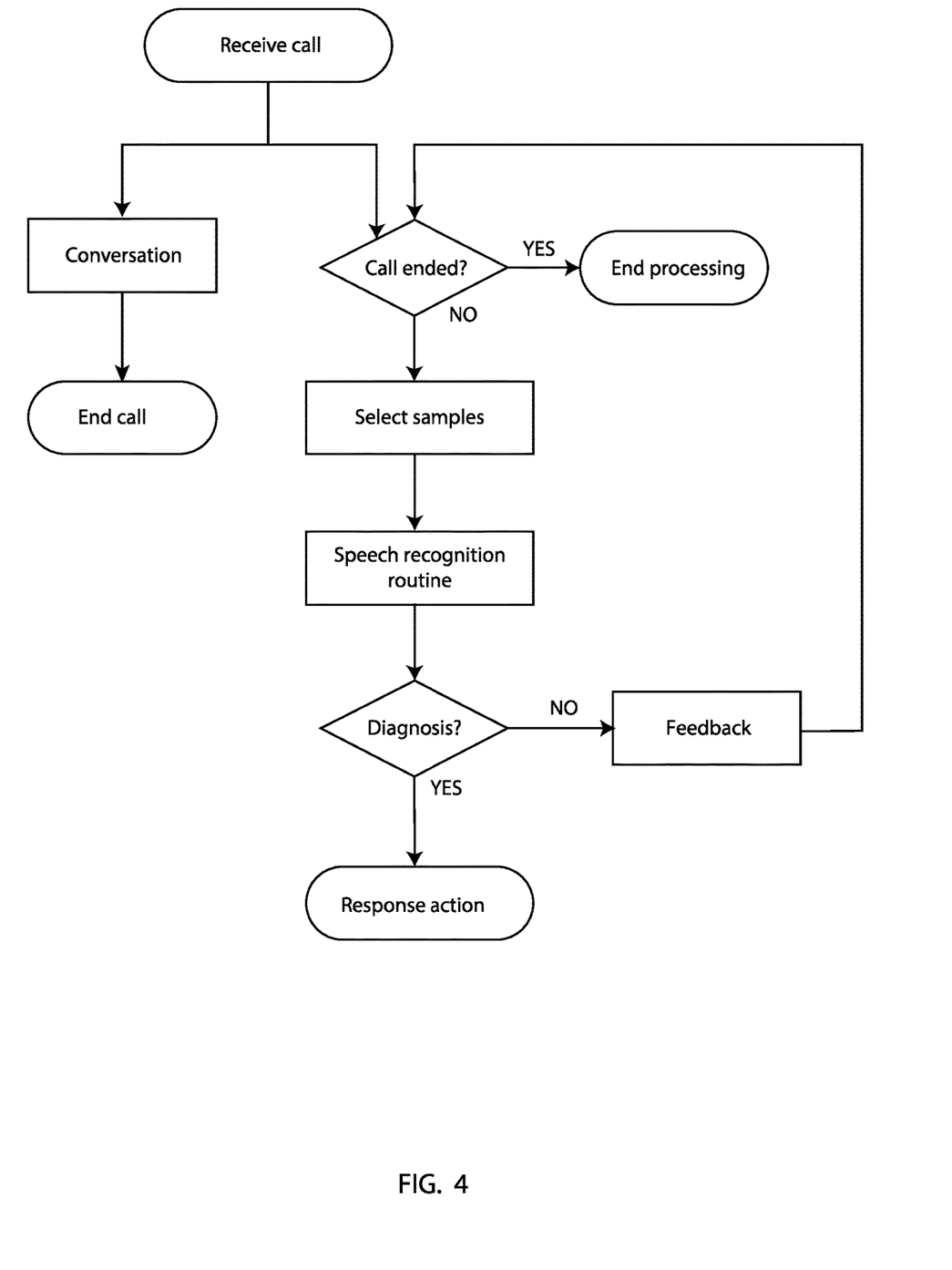
FIG. 4 shows a flowchart for assisting a medical call taker.

FIG. 4 shows a flowchart for assisting a medical call taker according to the third aspect of the invention.

The anomaly routine is omitted in the method, and the set of samples are processed one after the other by the audio recognition routine, and the diagnosis routine respectively.

Figure 5A:
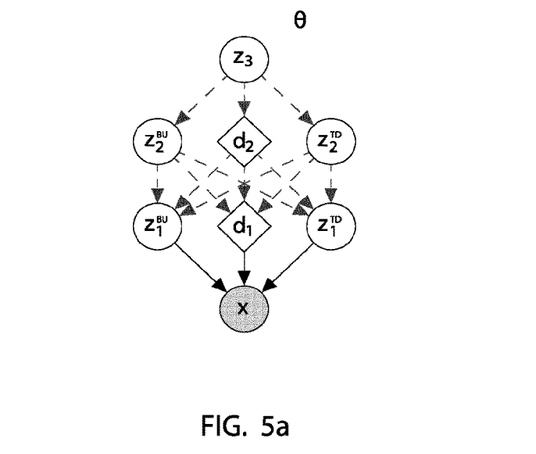
FIG. 5a shows a specific model for a decoder.

FIG. 5a shows a specific model for a decoder.

Figure 5B:
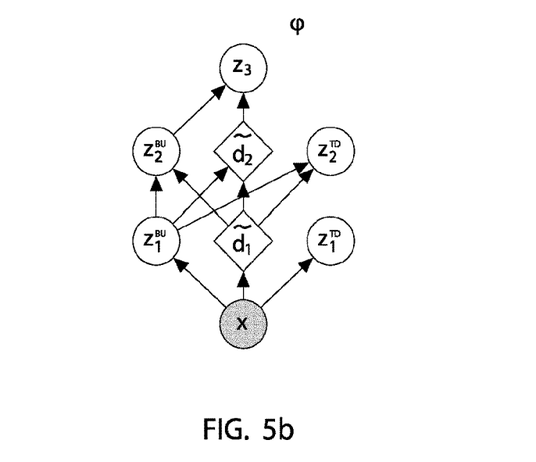
FIG. 5b shows a specific model for an encoder.

FIG. 5b shows a specific model for an encoder.

Both the decoder and encoder may be used for the processing routines illustrated in both FIGS. 2 and 4 respectively. The model defined by the decoder and encoder shown in FIGS. 5a-5c constitutes a bidirectional inference variational auto-encoder (BIVA).

In FIG. 5a, the decoder comprises a hierarchy having three layers. The top layer (third layer) having one random variable $z_3$, which is distributed according to a probability distribution. Typically, a normal distribution (Gaussian) may be used. The parameters of the probability distribution (mean and variance in the case of a normal distribution) may be determined by means of a neural network—one neural network may be used for each. Other statistically learned models may also be used to define the random variable.

More than three layers may be used and in the following, the number of layers is arbitrary, and a specific layer may be referred to using an index number.

For the layer below the top layer, i.e. the second layer, as well as the bottom layer, i.e. the first layer, it can be seen that the random variable of the respective layer is split in two components ($z_{i+1}^{BU}$, $z_{i+1}^{TD}$). The superscript BU refers to a bottom-up encoder path, and the superscript TD refers to a top-down encoder path (the encoder will be explained in connection with FIG. 5b).

The decoder may have a deterministic top-down path $d_{L-1}, \ldots, d_1$ (which may be parameterized with neural networks), and receives as input at each layer i of the hierarchy the random variable $z_{i+1}$.

This may be done by defining a fully convolutional model and concatenating ($z_{i+1}^{BU}$, $z_{i+1}^{TD}$) and $d_{i+1}$ along the features' dimension.

$d_i$ can therefore be seen as a deterministic variable that summarizes all the relevant information coming from the random variables higher in the hierarchy, $z_{>i}$.

Figure 5C:
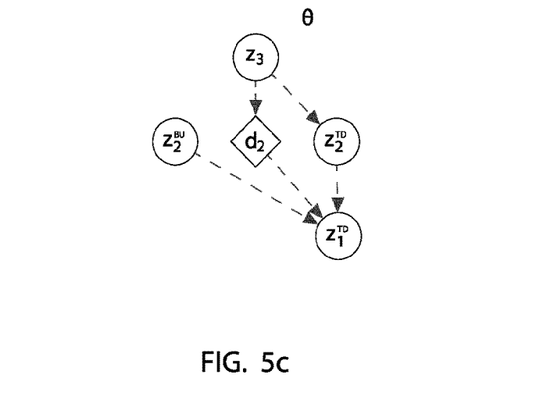
FIG. 5c shows a top-down path of the encoder.

In FIGS. 5a-5c dotted lines shows deterministic parameters being shared within the decoder or between the decoder and encoder.

The random variables $z_i^{TD}$ and $z_i^{BU}$ are conditioned on all the information in the higher layers, and are conditionally independent given $z_{>i}$.

The joint distribution (prior probability distribution) $p_\theta(x, z)$ of the decoder is given by:

$$p_\theta(x, z) = p_\theta(x \mid z) p_\theta(z_L) \prod_{i=1}^{L-1} p_\theta(z_i \mid z_{>i})$$

where $\theta$ refers to the parameters of the decoder, i.e. in the case neural networks are used to define the random variables (or the probability distributions for the random variables in the hierarchy), the parameters may be the weights of the neural networks.

$p_\theta(x|z)$ is a first factor defined as a first probability distribution of the observable variable x conditioned on the set of random variables, i.e. z.

$p_\theta(z_L)$ is a second factor defined as a second probability distribution of the random variable of the top layer $z_L$ (with index i=L) of the decoder. In FIG. 5a, L=3.

$$\prod_{i=1}^{L-1} p_\theta(z_i \mid z_{>i})$$

is a third factor defined as the product of sequence $$\prod_{i=1}^{L-1}$$

for the probability distributions for the random variables of the set of random variable for the decoder—the random variable of each respective element in said product of sequence is conditioned on the random variable of one or more of the higher layers. For example for index i=2, the random variable $z_2$ may be conditioned on the random variable $z_3$ or $z_4$ or higher. The condition may also be on several of higher laying random variables, i.e. $z_3$ or $z_4$ for example. For index or element i=L−1 the random variable $z_{L-1}$ is only conditioned on the top random variable $z_L$.

The elements in the product sequence may be factored out as $p_\theta(z_i|z_{>i})=p_\theta(z_i^{BU}|z_{>i}) p_\theta^{TD}/z_{>i})$, first factor defined as the conditional probability distributions for the bottom-up random variables (where information/data goes from the bottom towards the top of the hierarchy). And a second factor defined as the conditional probability distributions for the top-down random variables (where information/data goes from the top towards the bottom of the hierarchy).

The probability distributions may have diagonal covariance, with one neural network for the mean and another neural network for the variance.

Since the $z_{i+1}^{BU}$ and $z_{i+1}^{TD}$ variables are on the same level in the decoder and of the same dimensionality, all the deterministic parameters going to the layer below are shared.

Specifically, the decoder has a top-down path going from $z_L$ through the intermediary random variables to x. Between each layer there is a ResNet block with M layers set up. Weight normalization is applied in all neural network layers.

The neural network function (a function of decoder parameters θ) of ResNet layer j associated with layer i is denoted $f_{i,j}$.

The feature maps are written as $d_{i,j}$. The decoder routine can then be iterated as $z_L \sim N(0, I)$ and i=L−1, L−2, . . . , 1:

$$d_{i,0} = z_{i+1}$$
$$d_{i,j} = \left(f_{\theta_{i,j}}(d_{i,j-1}); d_{i+1,j}\right) \text{ for } j = 1, \ldots, M$$
$$z_i = \mu_{\theta,i}(d_{i,M}) + \sigma_{\theta,i}(d_{i,M}) \otimes \epsilon_i,$$

In FIG. 5b, the encoder comprises a hierarchy having three layers.

Due to the nonlinearities in the neural networks that parameterize the decoder, the exact posterior distribution $p_\theta(z|x)$ is intractable and needs to be approximated. A variational distribution (probability distribution for approximating a posterior probability distribution) $q_\phi(z|x)$ may be defined for this.

A bottom-up (BU) and a top-down (TD) encoder path are defined, and which are computed sequentially when constructing the posterior approximation for each data point x.

The variational distribution over the BU random variables depends on the data x and on all BU variables lower in the hierarchy, i.e. $q_\phi(z_i^{BU}|x,z_{<i}^{BU})$—alternatively, the condition may be on a fewer number of BU variables lower in the hierarchy such as only the BU variable in the layer below the layer of the respective index i. ϕ denotes all the parameters of the BU path. $z_i^{BU}$ may have a direct dependency only on the BU variable below, i.e. $z_{i-1}^{BU}$.

The dependency on $z_{i-1}^{BU}$ may be achieved, similarly to the decoder, through a deterministic bottom-up path $\tilde{d}_1, \ldots, \tilde{d}_{L-1}$.

The TD variables as well depend on the data and the BU variables lower in the hierarchy through the BU encoder path, but also on all variables above in the hierarchy through the TD encoder path in FIG. 5c. The variational approximation over the TD variables is thereby $q_{\phi, \theta}(z_i^{TD}|x,z_{<i}^{BU}, z_{>i}^{BU}, z_{>i}^{TD})$.

All the parameters of the TD path may be shared with the decoder, and are therefore denoted as θ whereas the parameters of the encoder are denoted ϕ. The encoder may be factorized as follows:

$$q_\phi(z \mid x) = q_\phi(z_L \mid x, z_{<L}^{BU}) \prod_{i=1}^{L-1} q_\phi(z_i^{BU} \mid x, z_{<i}^{BU}) \, q_{\phi,\theta}(z_i^{TD} \mid x, z_{<i}^{BU}, z_{>i}^{BU}, z_{>i}^{TD}),$$

i.e. the random variables z are conditionally distributed on the observable variable x according to a probability distribution $q_\phi(z|x)$ for approximating a posterior probability distribution.

The variational distributions over the BU and TD random variables may be Gaussians whose mean and diagonal covariance may be parameterized with neural networks that take as input the concatenation over the feature dimension of the conditioning variables.

The first factor $q_\phi(z_L|x,z_{<L}^{BU})$ may be defined as a first probability distribution of the random variable of the top layer of said encoder conditioned on the observable variable and the respective random variable of the bottom-up path below the top layer. The conditioned may further be on all of the respective random variable of the bottom-up path below the top layer—or it may exclude some of the random variables closet to the bottom of the hierarchy.

The second factor:

$$\prod_{i=1}^{L-1} q_\phi(z_i^{BU} \mid x, z_{<i}^{BU}) \, q_{\phi,\theta}(z_i^{TD} \mid x, z_{<i}^{BU}, z_{>i}^{BU}, z_{>i}^{TD})$$

may be defined as the product of sequence of the products between the probability distributions for the random variables of the bottom-up path $q_\phi(z_i^{BU}|x,z_{<i}^{BU})$ and the probability distributions $q_{\phi, \theta}(z_i^{TD}|x,z_{<i}^{BU}, z_{<i}^{BU}, z_{>i}^{BU}, z_{>i}^{TD})$ for the random variables of the top-down path.

The respective random variable of the bottom-up path for a given index (or element) in the product of sequence is conditioned on the observable variable and the respective random variable of the bottom-up path for a lower index than the given index.

The respective random variable of the top-down path for a given index in the product of sequence is conditioned on
the observable variable,
at least one respective random variable of the bottom-up path, and
the respective random variable of the top-down path for a higher index than the given index.

The respective random variable of the top-down path for a given index in the product of sequence may be conditioned on a random variable of the bottom-up path for a higher index than said given index and a random variable of the bottom-up path for a lower index than said given index, such that all of the random variables of the bottom-up path except for the one of the given index.

Training of encoder and decoder may be performed, as for variational auto encoders, by maximizing the evidence lower bound (ELBO) with stochastic backpropagation and the reparameterization trick:

$$\log p_\theta(x) \geq \mathbb{E}_{q_\phi(z|x)}\left[\log \frac{p_\theta(x, z)}{q_\phi(z \mid x)}\right] \equiv \mathcal{L}(\theta, \phi)$$

In the standard ELBO from the above, the main contribution to the expected log-likelihood term is coming from averaging over the variational distribution of the lower level random variables. This will thus emphasize low-level statistics.

When performing anomaly detection with the specific encoder and decoder shown in FIGS. 5a-5c and mentioned above, the contribution from the higher layers may be emphasized.

The evidence lower bound for the anomaly detection is a function of the posterior probability distribution (or the approximation thereof) $q_\phi(z_{>k}|\chi)$ as well as the prior probability distribution $p_\theta(z_{>k})$:

$$\mathcal{L}^{>k} = \mathbb{E}_{p_\theta(z_{\leq k}|z_{>k})q_\phi(z_{>k}|x)}\left[\log \frac{p_\theta(x \mid z)p_\theta(z_{>k})}{q_\phi(z_{>k} \mid x)}\right],$$

With respect to the prior probability distribution, it is for the random variables for the layers higher than k, i.e. the random variables of the lower variables are excluded. The choice of k may for example be 3 such that for a hierarchy with 6 layers, the prior probability distribution is for the random variables of the fourth, fifth and sixth layer. Thus, k may be seen as a layer number defining a specific layer between the top and bottom of the hierarchy. The layer number may correspond to the middle layer or a layer closer to the middle layer than the top or bottom.

It may be so that only one variable in the layer at or lower than k is excluded, i.e. for example only the random variable of the first or second layer is excluded and the distribution is for the other random variables of the hierarchy. In general, the prior probability distribution is for the random variables of the hierarchy excluding at least one random variable from one of the bottom two layers or the bottom three layers or the bottom four layers.

With respect to the posterior probability distribution, it is for the random variables for the layers higher than k. The random variables are conditioned on the observable variable x. The choice and function of k may be the same as for the prior probability distribution.

The random variables may be said to belong to a set of random variables defined as $z=z_1, z_2, z_3, \ldots, z_L$ with $z_i=(z_i^{BU}, z_i^{TD})$.

The computation of $L^{>k}$ is approximated with Monte Carlo integration.

Sampling from $P_\theta(z_{\leq k}|z_{>k})q_\phi(z_{>k}\chi)q_\phi(z_{>k}|\chi)$ can be performed by obtaining samples $\hat{z}>k$ from the encoder that are then used to sample $\hat{z}_{\leq k}$ from the conditional prior $p_\theta(z_{\leq k}|\hat{z}_{>k})$.

By only sampling the top L-k variables from the variational approximation, there is relied only on the high-level semantics encoded in the highest variables of the hierarchy when evaluating this metric, and not on the low-level statistics encoded in the lower variables.

Below is a list of reference signs used in the detailed description of the invention and in the drawings referred to in the detailed description of the invention.
- 10 Injured person
- 12 Caller
- 14 Medical call taker
- 16 Cell tower
- 18 Mobile phone
- 20 Receiver
- 22 Processing unit
- 24 Display
- 26 Public safety answering point

The invention claimed is:

1. A method for assisting an interviewing party in deciding a response action in response to an interview between said interviewing party and an interviewee party, said method comprising the steps of:
    providing a processing unit and inputting the voice of said interviewee party into said processing unit as an electronic signal,
    processing said electronic signal by means of said processing unit in parallel with said interview taking place, said processing lasting the duration of said interview or until said response action being decided by said interviewing party,
    said processing including:
    separating said electronic signal into a sequence of samples in the time domain or a domain representative of the frequency contents of said electronic signal,
    said processing further including:
    a) an anomaly routine comprising a statistically learned model, and
    by means of said statistically learned model determining:
        a respective number of samples of said sequence of samples being an anomaly of said statistically learned model or
        said respective number of samples being a normality of said statistically learned model,
    b) when said respective number of samples being determined as an anomaly of said statistically learned model:
        returning to said anomaly routine for processing a subsequent number of samples of said sequence of samples,
    c) when said respective number of samples being determined as a normality of said statistically learned model:
        providing an audio recognition model and detecting an audio feature of said respective number of samples by means of said audio recognition model,
        providing an action prediction model and analyzing said audio feature by means of said action prediction model for determining an expected response action, providing a display or a speaker, and presenting said expected response action to said interviewing party by means of said display or said speaker for assisting said interviewing party, returning to said anomaly routine for processing a subsequent number of samples of said sequence of samples by said anomaly routine.

2. A method of assisting an interviewing party in deciding a response action in response to an interview between said interviewing party and an interviewee party:

providing a processing unit and inputting the voice of said interviewee party into said processing unit as an electronic signal, processing said electronic signal by means of said processing unit in parallel with said interview taking place, said processing lasting the duration of said interview or until said response action being decided by said interviewing party, said processing including:

separating said electronic signal into a sequence of samples in the time domain or a domain representative of the frequency contents of said electronic signal, said processing further including:

a) an audio recognition routine including an audio recognition model for detecting an audio feature of a respective number of samples of said sequence of samples by means of a first statistically learned model, said audio recognition routine returning a first audio output representing the detected audio feature of said respective number of samples, b) an action prediction routine including a analyzing model for analyzing said first audio output by means of a second statistically learned model, said action prediction routine returning a feedback to said interviewing party, returning to said audio recognition routine and said action prediction routine for processing a respective subsequent number of samples of said sequence of samples by said audio recognition routine and said action prediction routine for determining an expected response action based on said respective interval and said respective subsequent interval, and presenting said expected response action to said interviewing party by means of a display or a speaker.

3. The method according to claim 1, comprising inputting the voice of said interviewing party into said processing unit.

4. The method according to claim 1, providing feedback to said interviewing party during said processing by means of said display or said speaker.

5. The method according to claim 4, said feedback constituting negative feedback when said respective number of samples being detected as an anomaly of said statistically learned model.

6. The method according to claim 5, said negative feedback being indicative of said processing taking place.

7. The method according to claim 1, the random variables of said set of random variables being divided into a bottom-up path and a top-down path.

8. The method according to claim 1, said decoder comprising a deterministic variable for summarizing information from random variables higher in said decoder hierarchy.

* * * * *